United States Patent [19]

Yui et al.

[11] Patent Number: 5,264,150
[45] Date of Patent: Nov. 23, 1993

[54] OPTICALLY ACTIVE ALCOHOL, PROCESS FOR PRODUCING SAME AND LIQUID CRYSTAL COMPOUND USING SAME

[75] Inventors: Tomoyuki Yui, Nagareyama; Hiroshi Mineta, Tsukuba; Masahiro Johno, Tsukuba; Yoshihisa Arai, Tsukuba, all of Japan

[73] Assignee: Mitsubishi Gas Chemical Company, Inc., Tokyo, Japan

[21] Appl. No.: 788,164

[22] Filed: Nov. 5, 1991

[30] Foreign Application Priority Data

Nov. 5, 1990 [JP] Japan .................................. 2-297125
Nov. 28, 1990 [JP] Japan .................................. 2-322462

[51] Int. Cl.$^5$ .................... C09K 19/20; C09K 19/12; C07C 41/00
[52] U.S. Cl. ........................ 252/299.64; 252/299.01; 252/299.65; 252/299.66; 252/299.67; 568/661
[58] Field of Search ............... 252/299.01, 299.64, 252/299.65, 299.66, 299.67; 359/103, 104, 91; 568/626, 630, 631, 642, 645, 647, 649, 661

[56] References Cited

U.S. PATENT DOCUMENTS 5,078,477 1/1992 Jono et al. .................. 359/91
5,108,650 4/1992 Koden et al. ............. 252/299.01

FOREIGN PATENT DOCUMENTS 0327349 9/1989 European Pat. Off. .
64-03154 1/1989 Japan .

Primary Examiner—Robert L. Stoll
Assistant Examiner—Shean C. Wu
Attorney, Agent, or Firm—Sherman and Shalloway

[57] ABSTRACT

A liquid crystal compound represented by formula (II)

$$R-X-(C_6H_4)_K-COO-(C_6H_4)_L-COO-\overset{CF_3}{\underset{|}{C^*}}H(CH_2)_mOC_nH_{2n+1} \quad (II)$$

wherein R denotes a linear alkyl group having 6 to 14 carbon atoms, X denotes a single bond or an oxygen atom, K and L are independently 1 or 2, m is an integer of 5 to 7, n is an integer of 1 to 4, and C* denotes an asymmetric carbon atom, said compound having an antiferroelectric phase. This liquid crystal compound is produced by using a novel optically active alcohol represented by formula (I)

$$\underset{|}{\overset{OH}{CF_3C^*}}H(CH_2)_mOC_nH_{2n+1} \quad (I)$$

12 Claims, 8 Drawing Sheets

OPTICALLY ACTIVE ALCOHOL, PROCESS FOR PRODUCING SAME AND LIQUID CRYSTAL COMPOUND USING SAME

DETAILED DESCRIPTION OF THE INVENTION

This invention relates to a novel optically active alcohol, a process for producing same and a liquid crystal compound using same. More specifically, this invention relates to a novel optically active alcohol having a trifluoromethyl group on an asymmetric carbon atom and an alkoxy group in the end, a process for producing same and a liquid crystal compound using said alcohol.

PRIOR ART

Liquid crystal display devices have been to date used as various small-screen devices because a voltage is low, an electric power consumed is low and thin display is possible. Since the liquid crystal display devices have, however, recently found use in the fields of information, office automation appliances, television, etc., high-performance, large-sized liquid crystal display devices having higher resolution and higher display qualities than the ordinary CRT display devices have been increasingly demanded rapidly.

Nevertheless, so far as the present nematic liquid crystals are used as display devices, even active matrix liquid crystal display devices employed in liquid crystal television sets have difficulty to produce a large screen with low cost owing to intricacy of their production process and their low yields. Meanwhile, simple matrix STN liquid crystal display devices are not necessarily easy to drive the large screen with high quality, and the response time is also limited. Under the circumstances, at the present stage, the nematic liquid crystal display devices cannot be said to meet the demand for the high-performance, large-sized liquid crystal display devices.

PROBLEMS THE INVENTION AIMS TO SOLVE

On the other hand, liquid crystal display devices using ferroelectric liquid crystal compounds arouse interest as liquid crystal display devices having high-speed response. Surface stabilized ferroelectric liquid crystal (SSFLC) devices reported by N. A. Clark and S. T. Lagerwall are noteworty in that they have high-speed response and a wide viewing angle that have not ever been provided [N. A. Clark and S. T. Lagerwall, Appl. Phys. Lett. 36(1980) 899].

Switching characteristics of said SSFLC devices have been studied in detail, and many ferroelectric liquid crystal compounds have been proposed to optimize various properties.

Said SSFLC devices have not been put to practical use, however, because of various factors that since threshold characteristics are not sufficient, contrast is poor, high-speed response is not realized, alignment is destroyed by mechanical shock and is hardly recovered, and so forth.

Separately, devices of switching mechanism different from SSFLC devices have been also developed at the same time. Tristable switching of liquid crystal compounds having an antiferroelectric phase (hereinafter referred to as "antiferroelectric liquid crystal compounds") are one of the new switching mechanisms (Japanese Journal of Applied Physics, vol. 27, No.5, p. L729, 1988).

Antiferroelectric liquid crystal devices (devices using antiferroelectric liquid crystal compounds) have three stable states, i.e., two uniform states (Ur, U1) observed in the ferroelectric liquid crystal devices and a third state. The very third state is an antiferroelectric phase reported by Chandani, et al (Japanese Journal of Applied Physics, vol. 28, p. L1261, 1989 and Japanese Journal of Applied Physics, vol. 28, p. L1265, 1989).

Such tristable switching is the first characteristic feature of the antiferroelectric liquid crystal devices. The second characteristic feature of the antiferroelectric liquid crystal devices is a sharp threshold against an applied voltage. The third characteristic feature thereof is memory effect. Liquid crystal display devices having high-speed response and good contrast can be realized by utilizing these excellent characteristic features.

Another great characteristic feature is that a layer structure is easily switched by an electric field (Japanese Journal of Applied Physics, vol. 28, p. L119, 1989, and Japanese Journal of Applied Physics, vol. 29, p. L111, 1990). As a result, it becomes possible to realize less defective liquid crystal display devices having an alignment self-recovering ability.

As the antiferroelectric liquid crystal compound, those described in Japanese Laid-open Patent Appln. (Kokai) Nos. 213390/1989, 316339/1989, 316367/1989, 316372/1989 and 28128/1990 and Liquid Crystals, vol. 6, No. 2, p. 167, 1989 are known. Meanwhile, studies over the antiferroelectric liquid crystal compounds have just started, and antiferroelectric liquid crystal compounds known to date are few.

In the field of the aforesaid ferroelectric liquid crystals, for liquid crystals to show ferroelectricity, it is inevitable that liquid crystal molecules are optically active (e.g., "Journal of Synthetic Organic Chemistry Association", Jono & Fukuda, 47 (6), 568, 1989).

In this field, optically active materials such as 2-butanol, 2-octanol, 2-methyl-1-butanol and amino acid derivatives have been used as an optically active source. Characteristics of materials obtained by using such known optically active substances are, however, limited and not sufficiently satisfactory. New optically active substances are therefore demanded.

In the field of ferroelectric liquid crystals, ferroelectric liquid crystals that use the following optically active alcohols having a fluoroalkyl group on an asymmetric carbon atom as an optically active source have lately been proposed (the asymmetric carbon atom is indicated at "C*").

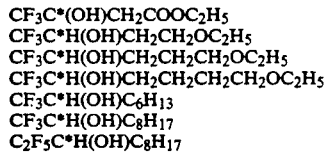

Ferroelectric liquid crystals using these optically active alcohols are described in, e.g., Japanese Laid-open Patent Appln. (Kokai) Nos. 3154/1989, 316339/1989, 316367/1989, 316372/1989, 225434/1990 and 229128/1990.

Since the ferroelectric liquid crystals using the above alcohols have a highly negative fluorine atom on an asymmetric carbon atom, they allow great spontaneous polarization and provides relatively high-speed response. Moreover, the liquid crystals using $CF_3C^*H(OH)C_6H_{13}$, $CF_3C^*H(OH)C_8H_{17}$ and $C_2F_5C^*H(OH)C_8H_{17}$ among the above alcohols are deemed to easily give ferroelectric liquid crystals having an antiferroelectric phase. For this reason, these alcohols attract attention as very characteristic alcohols.

The alcohols having the fluorinated structure on the asymmetric carbon atom in the molecule (hereinafter referred to at times as "fluorinated alcohols") thus arouse interest as a starting material to produce ferroelectric liquid crystals having an antiferroelectric phase (hereinafter referred to at times as "antiferroelectric liquid crystals"). The antiferroelectric liquid crystals formed by using the aforesaid known fluorinated alcohols are nevertheless still insufficient in response speed, practical temperature range, etc. Such fluorinated alcohols as to give liquid crystals having better performance has been longed for.

Known methods for producing the aforesaid optically active alcohols are intricate and not said to be effective. For instance, a known method for producing an optically active alcohol represented by the formula $CF_3C^*H(OH)(CH_2)_4OC_2H_5$ requires the following many steps.

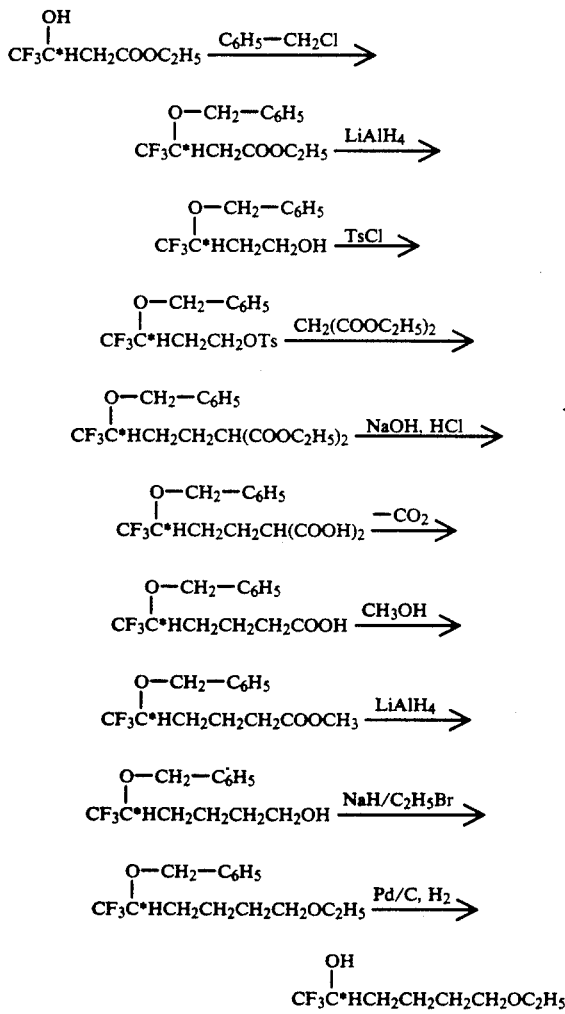

In the above reaction steps, "TsCl" denotes p-toluenesulfonic acid chloride, and "Ts" denotes a p-toluenesulfonyl group.

It is thus a first object of this invention to provide a novel liquid crystal compound having an anti-ferroelectric phase.

A second object of this invention is to provide a liquid crystal compound which can be used in a liquid crystal display device having tristable switching, sharp threshold and good memory effect.

A third object of this invention is to provide a high-performance liquid crystal compound that can be used in a large-sized liquid crystal display device having high-speed response.

A fourth object of this invention is to provide a novel optically active alcohol that is used to form the liquid crystal compound of this invention.

A fifth object of this invention is to provide a novel, industrially advantageous process for producing the optically active alcohol.

The other objects of this invention will be clarified from the following description.

MEANS FOR SOLVING THE PROBLEMS

According to the present inventors' studies, it is found that the objects and advantages of this invention can be achieved by a liquid crystal compound represented by formula (II)

$$R-X-(C_6H_4)_K-COO-(C_6H_4)_L-COO-C^*H(CH_2)_mOC_nH_{2n+1} \quad (II)$$

wherein R denotes a linear alkyl group having 6 to 14 carbon atoms, X denotes a single bond or an oxygen atom, K and L are independently 1 or 2, m is an integer of 5 to 7, n is an integer of 1 to 4, and C* denotes an asymmetric carbon atom.

It is further found that the objects and advantages of this invention can be achieved by an optically active alcohol represented by formula (I)

wherein m is an integer of 5 to 7, n is an integer of 1 to 4, and C* denotes an asymmetric carbon atom, which compound is used to form the liquid crystal compound of formula (II).

It is still further found that the objects and advantages of this invention can be achieved by a process for producing an optically active alcohol represented by formula (I)

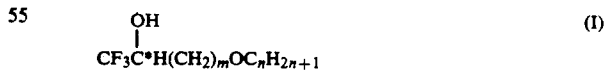

wherein m is an integer of 5 to 7, n is an integer of 1 to 4, and C* denotes an asymmetric carbon atom, which comprises (i) reacting a sulfonic acid ester represented by formula (I-1)

wherein W denotes a hydroxyl-protecting group, Y denotes a sulfonyl group, and C* denotes an asymmetric carbon atom, with a Grignard reagent represented by formula (I-2)

$$C_nH_{2n+1}O(CH_2)_pMgBr \quad (I\text{-}2)$$

wherein p-is an integer of 3 to 5, and n is an integer of 1 to 4, to obtain an ether compound represented by formula (I-3)

$$\underset{|}{\overset{O-W}{CF_3-C^*G(CH_2)_mOC_nH_{2n+1}}} \quad (I\text{-}3)$$

wherein W, n and C* are as defined above, and m is an integer of 5 to 7, and (ii) removing the hydroxyl-protecting group (W) of the ether compound of formula (I-3).

The liquid crystal compound, the optically active alcohol and the process for producing the optically active alcohol in this invention will be described in more detail.

[A] Liquid crystal compound of this invention

As described above, the liquid crystal compound of this invention is represented by formula (II).

$$R-X-(C_6H_4)_K-COO-(C_6H_4)_L-COO-\underset{|}{\overset{CF_3}{C^*H(CH_2)_mOC_nH_{2n+1}}} \quad (II)$$

The compound of formula (II) has the asymmetric carbon atom (C*) in the molecule, and —CF$_3$ is directly bonded to said carbon atom. In formula (II), R is a linear alkyl group having 6 to 14 carbon atoms, preferably 8 to 12 carbon atoms; X is a single bond or an oxygen atom;

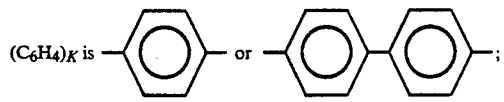

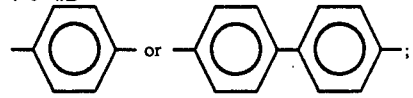

m is an integer of 5 to 7, especially preferably 5; and n is an integer of 1 to 4, preferably 2 or 3.

The liquid crystal compound of formula (II) is novel, and an example of a process for producing same is schematically shown below.

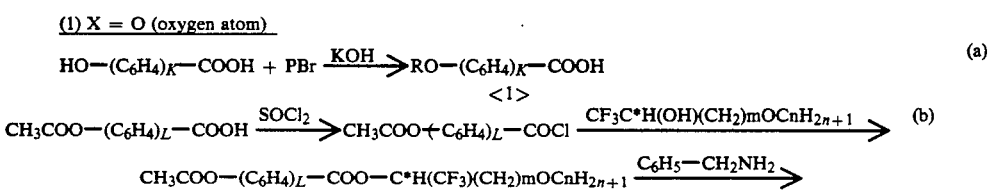

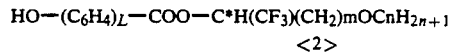

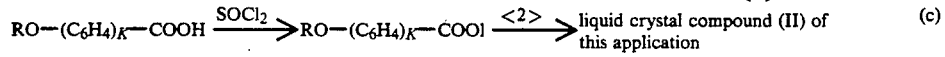

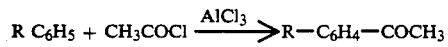

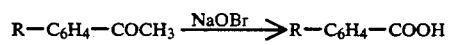

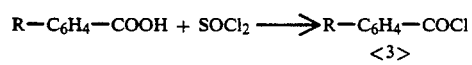

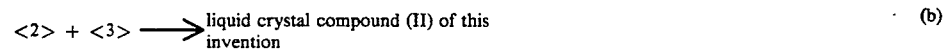

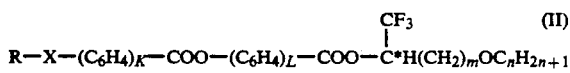

In formulas (1) and (2), R, K, L, m and n are as defined in formula (II), and R' is a linear alkyl group having 5 to 14 carbon atoms (while R is a linear alkyl group having 6 to 14 carbon atoms).

The number of carbon atoms of the alkyl group denoted by R in the above reaction schemes influences the phase transition temperature and the melting point of the liquid crystal. When the number of carbon atoms is too small, even a liquid crystal phase is not shown. When the number of carbon atoms is too large, a temperature of a chiral smectic C phase or an antiferroelectric phase useful as a switching device is by far higher than room temperature, and a melting point becomes high; they are practically unwanted. For this reason, the number of carbon atoms of R is 6 to 14, preferably 8 to 12.

To develop the antiferroelectric phase, m in formula (II) has to be 5 to 7. Moreover, n in C$_n$H$_{2n+1}$ of formula (II) does not influence properties of the resulting liquid crystal so much. However, to obtain a stable liquid crystal phase, n is 1 to 4, preferably 2 to 4.

[B] Optically active alcohol and process for producing same in this invention

The optically active alcohol of the following formula (I) which is used to produce the liquid crystal compound (II) of this invention is a novel compound.

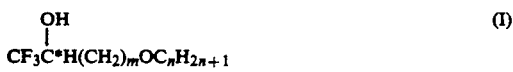

wherein m is an integer of 5 to 7, n is an integer of 1 to 4, preferably 2 to 4, and C* denotes an asymmetric carbon atom.

In accordance with this invention, the optically active alcohol of formula (I) is produced by step (i) of reacting a sulfonic acid ester of formula (I-1)

wherein W denotes a hydroxyl-protecting group, Y denotes a sulfonyl group, and C* denotes an asymmetric carbon atom, with a Grignard reagent represented by formula (I-2)

$$C_nH_{2n+1}O(CH_2)_pMgBr \quad (I-2)$$

wherein p is an integer of 3 to 5, and n is an integer of 1 to 4, to obtain an ether compound represented by formula (I-3)

wherein W, n and C* are as defined above, and m is an integer of 5 to 7, and step (ii) of removing the hydroxyl-protecting group (W) of the ether compound of formula (I-3).

Moreover, in accordance with this invention, the sulfonic acid ester of formula (I-1) used as a starting material is formed by step (a) of reducing optically active 4,4,4-trifluoro-3-hydroxybutyric acid ester represented by formula (I-4)

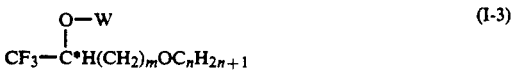

wherein A denotes a lower alkyl group, W denotes a hydroxyl-protecting group, and C* denotes an asymmetric carbon atom, to obtain an alcohol represented by formula (I-5)

wherein W and C* are as defined above, and step (b) of reacting the alcohol with a sulfonating agent.

Thus, in accordance with this invention, there is provided a process for producing an optically active alcohol of formula (I) by step (i)→step (ii), or step (a)→step (b)→step (i)→step (ii).

The process of this invention will be concretely described below in sequence from the step (a).

The optically active 4,4,4-trifluoro-3-hydroxybutyric acid ester of formula (I-4) which is a starting material in the step (a) can easily be obtained, for example, by asymmetrically reducing 4,4,4-trifluoroacetoacetic acid ester represented by the formula $CF_3COCH_2COOA$ (wherein A is a lower alkyl group, especially ethyl) to obtain optically active 4,4,4-trifluorobutyric acid ester represented by the formula $CF_3C^*H(OH)CH_2COOA$ and protecting the hydroxyl group.

Reduction of the 4,4,4-trifluoroacetic acid ester with bread yeast can easily give an R-form ester. Asymmetrical reduction of the 4,4,4-trifluoroacetic acid ester using a ruthenium-optically active phosphine complex as a catalyst can easily give both R-form and S-form esters (see Japanese Laid-open Patent Appln. (Kokai) No. 310847/1988).

Protection of the hydroxyl group can be conducted by a method known per se. The protecting agent can be any known protecting agent if it can remove the hydroxyl-protecting group (W) and convert the protected group into a hydroxyl group. Examples of the protecting agent are dihydropyran (DHP) and benzyl chloride.

Reduction of the ester moiety of the 4,4,4-trifluoro-3-hydroxybutyric acid ester represented by formula (I-4) can be carried out by a known method of reducing the ester moiety into —CH₂OH. A typical example thereof is a reducing method using lithium aluminum hydride (LiAlH₄).

Since the thus formed alcohol of formula (I-5) is a relatively unstable compound, it is used in the next step at once without purification.

Esterification of the resulting alcohol of formula (I-5) with the sulfonating agent can be conducted by an ordinary reaction of sulfonating —OH. For example, p-toluenesulfonic acid chloride (TsCl) is used as the sulfonating agent.

Meanwhile, in the step (i), the Grignard reagent of formula (I-2) being reacted with the sulfonic acid ester of formula (I-1) is easily formed by using an alkoxy alcohol obtained as schematically shown below.

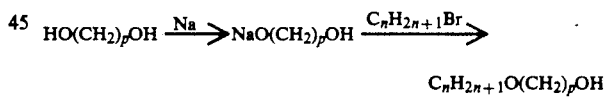

The thus obtained alkoxy alcohol is, as schematically shown below, brominated in a usual manner and then reacted with magnesium in a nitrogen stream to obtain a Grignard reagent of formula (I-2).

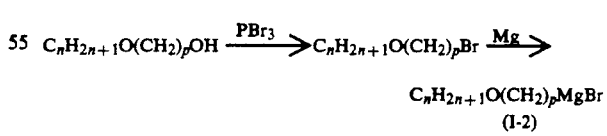

Then, the sulfonic acid ester of formula (I-1) and the Grignard reagent of formula (I-2) are subjected to a coupling reaction (step ii) to obtain an ether compound of formula (I-3).

In the coupling reaction, control of the reaction temperature is important, and at a temperature of lower than −15° C., the reaction is slowed down. At a temperature of higher than −5° C., a side reaction occurs frequently, and it is undesirous.

The optimum temperature is within a narrow range around −10° C., and it is advisable to keep the temperature during the reaction within ±2° C. In the coupling reaction, cuprous iodide is used as a catalyst. Its amount is 1 to 0.5 mol, preferably 0.2 to 0.35 mol per mol of the sulfonic acid ester (I-1) which is the reaction starting material. It is advisable to add cuprous iodide in small portions over the whole reaction time. The reaction time is 5 to 25 hours, preferably 8 to 14 hours.

EFFECTS OF THE INVENTION

Thus, in accordance with this invention, there are provided a novel optically active alcohol of formula (I) having a trifluoromethyl group on an asymmetric carbon atom and an alkoxy group in the end, which alcohol is useful as a starting material of ferroelectric liquid crystals, medicaments, agricultural chemicals and other functional materials, and an industrially advantageous process for producing the optically active alcohol of formula (I).

Moreover, in accordance with this invention, there is provided a novel liquid crystal compound of formula (II) using the optically active alcohol of formula (I) as a starting material, which compound has an antiferroelectric phase and is highly valuable as a liquid crystal display device owing to various excellent characteristics.

EXAMPLES

Figure 1:
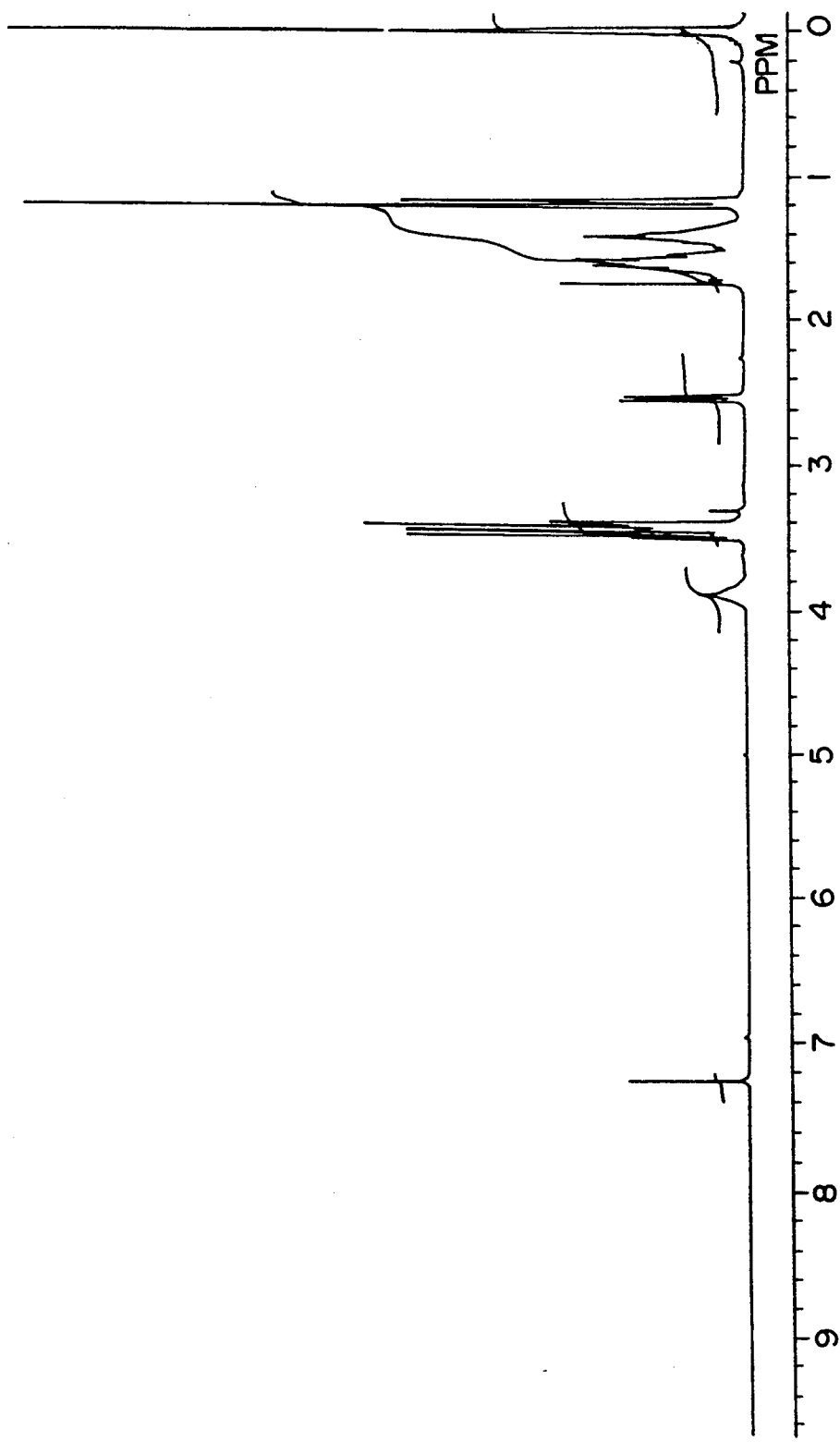
FIG. 1 is an NMR spectrum of 1,1,1-trifluoro-7-ethoxy-2-heptanol obtained in Example 1.

The following Examples illustrate this invention more specifically. This invention is however not limited thereto.

EXAMPLE 1

Production of R-(+)-1,1,1-trifluoro-7-ethoxy-2-heptanol (In formula (I), m=5, n=2)

(1) Protection of a hydroxyl group of ethyl 4,4,4-trifruolo-3-hydroxybutyrate with dihydropyran With stirring, 7 ml of conc. hydrochloric acid was added dropwise to a mixture of 33.4 g of R-(+)-ethyl 4,4,4-trifluoro-3-hydroxybutyrate and 22.6 g of dihydropyran under ice cooling. After the dropwise addition, stirring continued at room temperature for another 5 hours. The reaction mixture was poured into ice water, neutralized with sodium hydrogen carbonate, and then extracted with methylene chloride. After drying, the solvent was evaporated. The residue was distilled under reduced pressure of 6 mmHg to obtain 41.3 g of final ethyl 4,4,4-trifluoro-3-tetrahydropyranyloxybutyrate (1) (yield 85 %).

(2) Reduction of ethyl 4,4,4-trifluoro-3-tetrahydropyranyloxybutyrate with lithium aluminum hydride Fifty milliliters of an ether solution of 30.1 g of ethyl 4,4,4-trifluoro-3-tetrahydropyranyloxybutyrate (1) were added dropwise to an ether suspension of 4.2 g of lithium aluminum hydride over a period of 1.5 hours. The mixture was further refluxed for 30 minutes, and a mixed solution of 8 g of water and 50 ml of tetrahydrofuran was added dropwise under ice cooling. The solid was separated by filtration and extracted with ether. After drying, the ether was evaporated to obtain 28.1 g of 4,4,4-trifluoro-3-tetrahydropyranyloxybutyl alcohol (2) in a purity of 65%. Since the compound (2) was relatively unstable to heat and acid, said compound was only dried in pyridine with a molecular sieve 4A and used in the subsequent step.

(3) Conversion of 4,4,4-trifluoro-3-tetra hydropyranyloxybutyl alcohol into a sulfonic acid ester Fifty milliliters of a pyridine solution of 28.1 g of said compound (2) (purity 65%) were cooled to −10° C., and 23.3 g of p-toluenesulfonyl chloride was added, followed by stirring the mixture for 1.5 hours. Then, pyridine was evaporated at room temperature under reduced pressure, and the precipitated solid was dissolved in methylene chloride. The methylene chloride solution was then washed with an ammonium acetate saturated aqueous solution. After drying, methylene chloride was removed at room temperature, and low-boiling matters were removed under reduced pressure. The residue was then purified by silica gel column chromatography using benzene as a solvent to obtain a sulfonic acid ester (3) having a purity of 83% in a yield of 35% from ethyl 4,4,4-trifluoro-3-tetrahydropyranyloxybutyrate (1).

(4) Production of 3-ethoxy-1-bromopropane

Phosphorus tribromide (14.5 g) was slowly added dropwise to 16.8 g of 3-ethoxy-1-propanol. Thirty minutes later, the mixture was distilled in vacuo at 150° C. and 90 mmHg. Methylene chloride was added to the distillate, and the mixture was washed with a saturated sodium hydrogen carbonate aqueous solution. After drying, the solvent was removed, and the residue was distilled under reduced pressure to obtain 14.8 g of 3-ethoxy-1-bromopropane (4) having a purity of 94% (yield 55%).

(5) Production of 1,1,1-trifluoro-7-ethoxy-2-tetrahydropyranyloxyheptane

To 1.5 g of magnesium was added 10 ml of tetrahydrofuran under a nitrogen atmosphere. After magnesium was activated with a small amount of iodine, a solution of 9.4 g of the compound (4) in 20 ml of tetrahydrofuran was added dropwise at room temperature to prepare a Grignard reagent in a system. The solution was cooled to −10° C. and the sulfonic acid ester (3) was slowly added dropwise. One gram of copper iodide as a catalyst was added 14 times at a rate of one addition per hour. After the addition for about 14 hours, the reaction mixture was poured into 100 g of an aqueous solution of 4.4 g of ammonium acetate, and extracted with hexane and ether. After drying, the solvent was evaporated, 50 ml of ether was added to the residue, and the solution was added dropwise to an ether suspension of lithium aluminum hydride, followed by refluxing for 1 hour. After the reaction product was left to cool, water was added under ice cooling, and excess lithium aluminum hydride was decomposed. Subsequently, the solid was separated by filtration, and extracted with hexane and ether. After drying, the solvent was evaporated, and the residue was distilled in vacuo to obtain 4.5 g of a final product (5) having a purity of 70% (yield 54%).

(6) Production of 1,1,1-trifluoro-7-ethoxy-2-heptanol

One milliliter of conc. hydrochloric acid was added to 10 ml of a methanol solution of 4.5 g of the compound (5), and the mixture was left to stand overnight. The solution was added to a saturated sodium hydrogen carbonate aqueous solution, and the mixture was extracted with hexane and ether. After drying, the solvent was evaporated to obtain 2.2 g of a final compound in a purity of 86% (yield 72%). $[\alpha]_D^{28} = +12°$ (C=1.5, CHCl$_3$). FIG. 1 shows an NMR spectrum of final 1,1,1-trifluoro-7-ethoxy-2-heptanol.

(7) Using the optically active alcohol obtained in (6), the following liquid crystal compound was produced, and phase transition temperatures of said compound were measured as shown below.

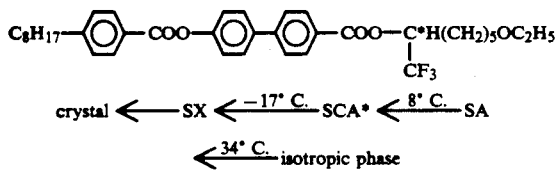

wherein S$_{CA}$* is an antiferroelectric chiral smectic C phase, S$_A$ is smectic A phase, and S$_X$ is an unidentified smectic phase.

Meanwhile, the temperature region of the S$_{CA}$* phase of the above compound is found to be far lower than that of the S$_{CA}$* phase of the following compound which is a known antiferroelectric liquid crystal similar to the above compound.

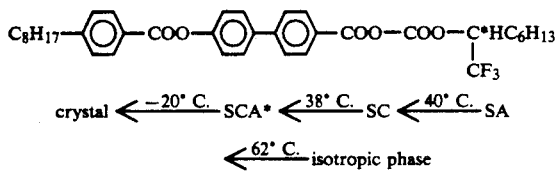

Accordingly, regarding the blend of the liquid crystals, the liquid crystal compound obtained by using the optically active alcohol of this invention can be used quite advantageously to expand the temperature region below room temperature.

EXAMPLE 2

Production of 4-(1-trifluoromethyl-6-ethoxyhexyloxycarbonylphenyl) 4'-octyloxybiphenyl-4-carboxylate (In formula (II), R=C$_6$H$_{17}$, X=O, K=2, L=1, m=5, n=2)

1) Production of 4-(4'-n-octyloxy)biphenylcarboxylic acid (1)

$$n-C_8H_{17}O-C_6H_4-C_6H_4-COOH \qquad (1)$$

4-(4'-Hydroxy)biphenylcarboxylic acid (10.5 g), 14.0 g of n-octyl bromide and 6.45 g of potassium hydroxide were added to a mixed solution of 1500 ml of ethanol and 200 ml of water, and the reaction was conducted under reflux for 10 hours. Further, 500 ml of water was added, and the mixture was stirred for 3 hours. After the reaction was over, the reaction mixture was acidified with conc. hydrochloric acid, and 500 ml of the solvent was evaporated. The residue was cooled to room temperature to obtain a white solid. The solid was thoroughly washed with water, and recrystallized with chloroform to obtain 12.0 g of a final product (1) as a white crystal.

2) Production of 4-acetoxy-1-(1-trifluoromethyl-6-ethoxyhexyloxycarbonyl)benzene (2)

$$CH_3COO-C_6H_4-COO-C^*H(CF_3)(CH_2)_5OC_2H_5 \qquad (2)$$

4-Acetoxybenzoic acid (3.5 g) was added to 25 ml of thionyl chloride, and the reaction was run under reflux for 10 hours. Subsequently, excess thionyl chloride was evaporated. Ten milliliters of pyridine and 50 ml of toluene were added, and 2.0 g of optically active 1,1,1-trifluoro-7-ethoxy-2-heptanol was added dropwise. After the dropwise addition, the mixture was refluxed for 4 hours, left to cool, and diluted with 500 ml of dichloromethane. The organic layer was washed with dilute hydrochloric acid, a 1N sodium hydroxide aqueous solution and water in this sequence, and dried over magnesium sulfate. The solvent was evaporated, and 1.9 g of a crude final product (2) was obtained.

3) Production of 4-hydroxy-1-(1-trifluoromethyl-6-ethoxyhexyloxycarbonyl)benzene (3)

$$HO-C_6H_4-COO-C^*H(CF_3)(CH_2)_5OC_2H_5 \qquad (3)$$

The crude product (1.9 g) of the above compound (2) was dissolved in 50 ml of ethanol, and 4 g of benzylamine was added dropwise. Further, after stirring was conducted at room temperature for 4 hours, the mixture was diluted with 500 ml of chloroform, washed with dilute hydrochloric acid and water in this sequence, and dried over magnesium sulfate. After the solvent was evaporated, the residue was isolated and purified by silica gel column chromatography to obtain 1.2 g of a final product (3).

4) Production of 4-(1-trifluoromethyl-6-ethoxyhexyloxycarbonylphenyl) 4'-n-octyl oxybiphenyl-4-carboxylate (4)

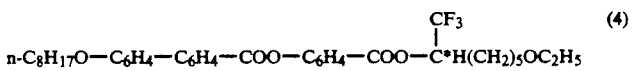

Figure 2:
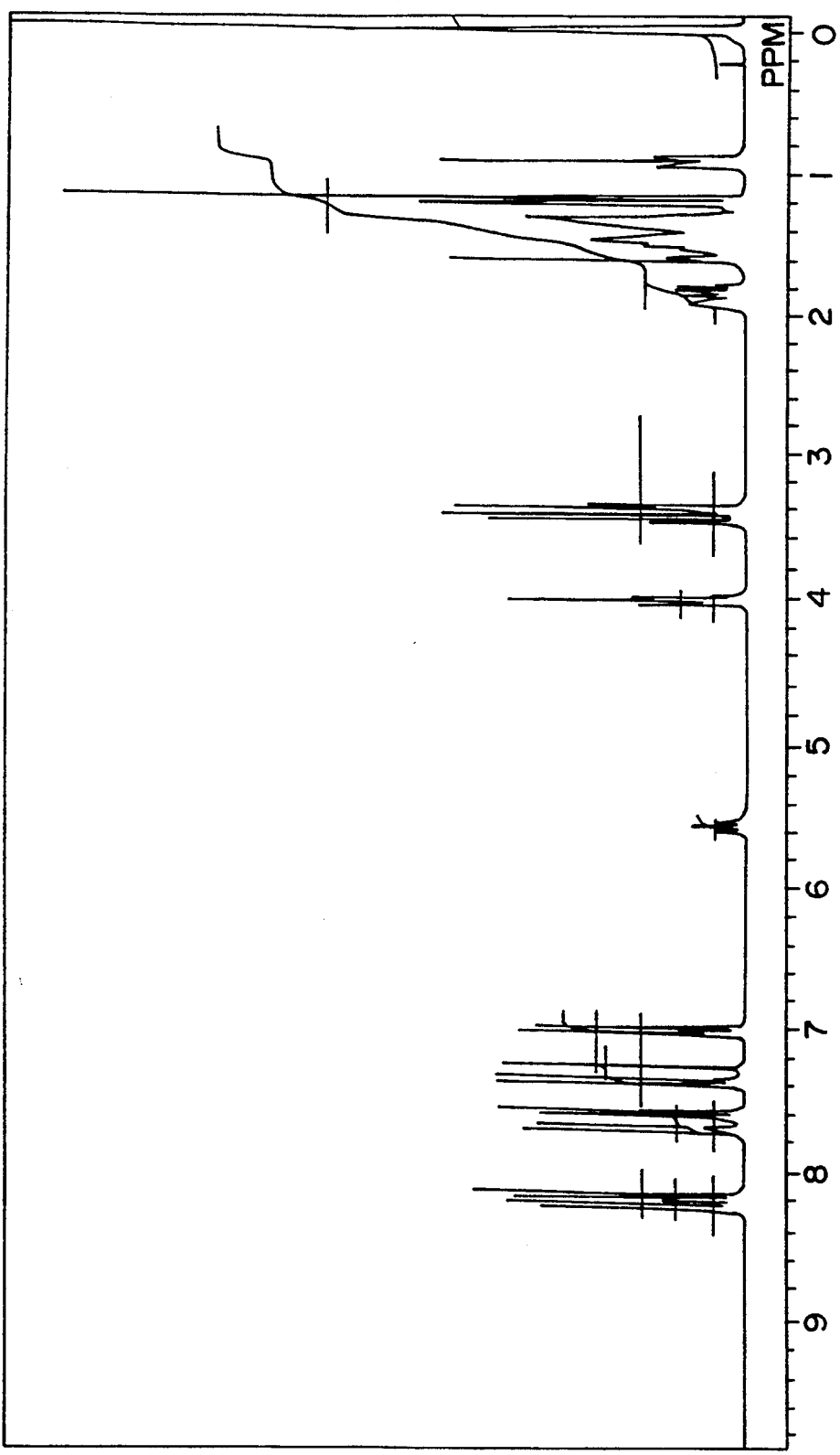
FIG. 2 is an NMR spectrum of a liquid crystal compound (4) in Example 2.

To 1.0 g of the above compound (1) was added 10 ml of thionyl chloride, and the mixture was refluxed with heating for 10 hours. After excess thionyl chloride was evaporated, 10 ml of pyridine and 60 ml of toluene were added, and 20 ml of a toluene solution of 0.5 g of the above compound (3) was added dropwise, followed by the reaction at room temperature for 10 hours. After the reaction, the reaction mixture was diluted with 500 ml of chloroform, and washed with dilute hydrochloric acid, a 1N sodium carbonate aqueous solution and water in this sequence. The organic layer was dried over magnesium sulfate. Subsequently, the solvent was evaporated and the solid was purified by silica gel column chromatography. The purified solid was then recrystallized with ethanol to obtain 0.8 g of a final product (4). An NMR spectrum of the final product (4) is shown in FIG. 2. Identification of phases was carried out by observation of a texture and measurement with DSC (differential scanning calorimeter).

Phase transition temperatures of the compound (4) of this invention are as follows. In the compound (4), an antiferroelectric phase was observed, but a chiral smectic C phase (S$_{C*}$) was not.

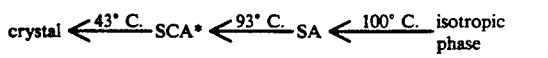

wherein S$_A$ and S$_{CA*}$ are a smectic A phase and an antiferroelectric phase, respectively.

5) A liquid crystal cell (a cell thickness 3 micrometers) with an ITO electrode having a rubbed polyimide thin film was filled with the compound (4) in an isotropic phase. The cell was slowly cooled at a rate of 1.0° C. per minute, and the liquid crystal was aligned in a S$_A$ phase. The cell was disposed between intersecting deflection plates such that the layer direction of the liquid crystal was parallel to an analyzer or a polarizer. A triangular wave voltage of ±40 V and 0.2 Hz was applied to the cell and change in transmittance was measured by a photomultiplyer. As a result, a double hysteresis peculiar to the antiferroelectric phase was observed in a temperature region of from 90° C. to 43° C.

Figure 3:
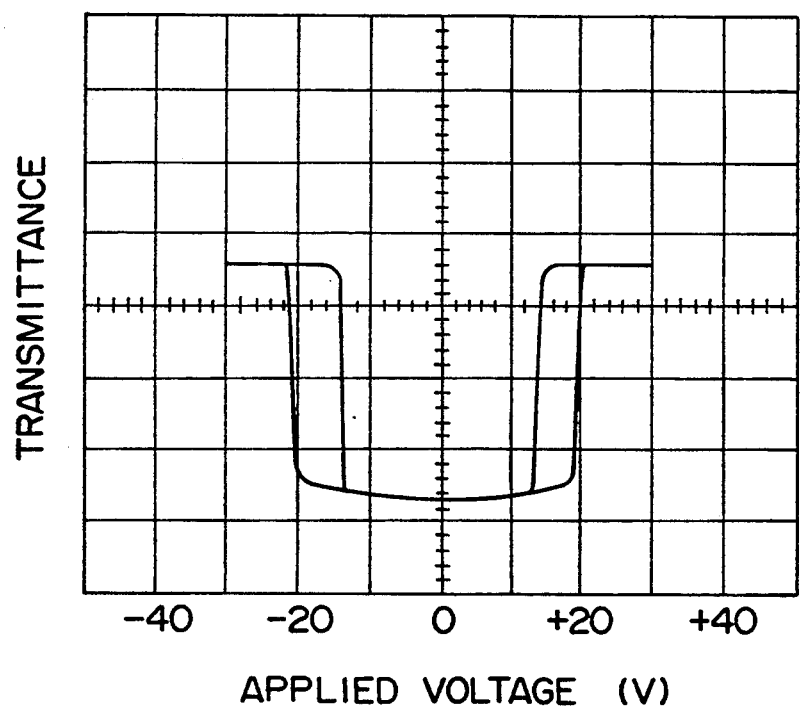
FIG. 3 is an optical response hysteresis of a liquid crystal compound (4) in Example 2.

An optical response hysteresis at 80° C. is shown in FIG. 3.

EXAMPLES 3 AND 4

In the same way as in Example 2, a compound of formula n—C$_q$H$_{2q+1}$O—C$_6$H$_4$—C$_6$H$_4$—COO—C*H(CF$_3$)—(CH$_2$)$_5$OC$_2$H$_5$ wherein q is 9 or 12 was produced, and identification of phases was conducted by observation of a texture and measurement with DSC.

Phase transition temperatures of the compounds are as shown in Table 1. They were found to have an antiferroelectric phase.

In the same way as in 5) of Example 2, optical response of these compounds was measured, and they were found to have a double hysteresis peculiar to the antiferroelectric phase.

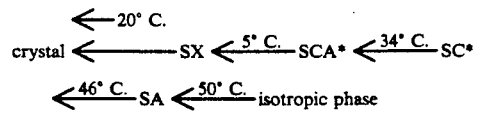

In the same way as in 5) of Example 2, optical response of this compound was measured, and a double hysteresis peculiar to an antiferroelectric phase was shown.

EXAMPLE 6

Production of 4-(1-trifluoromethyl-6-ethoxyhexyloxycarbonylbiphenyl) 4'-octylbenzoate (In formula (II), R=C$_8$H17, X=-(single bond), K=1, L=2, m=5, n=2)

1) Production of 4'-acetoxy-4-(1 trifluoromethyl-6-ethoxyhexyloxycarbonyl)biphenyl (1)

CH$_3$COO—C$_6$H$_4$—C$_6$H$_4$—COO—C*H(CF$_3$)(CH$_2$)$_5$OC$_2$H$_5$     (1)

Ten milliliters of thionyl chloride were added to 2.5 g of 4'-acetoxy-4-biphenylcarboxylic acid, and the mixture was refluxed for 6 hours. Excess thionyl chloride was then completely evaporated. The resulting acid chloride was dissolved in 50 ml of toluene, and 5 ml of pyridine was further added. To the solution was added dropwise 1.4 g of 1,1,1-trifluoro-7-ethoxy-2-heptanol. The mixture was refluxed for 18 hours with heating, and left to cool. One hundred milliliters of dichloromethane were added, and the mixture was washed with hydrochloric acid, a sodium hydroxide aqueous solution and water in this sequence. After drying, the solvent was removed, and the residue was purified by silica gel column chromatography to obtain 2.5 g of a final prod-

TABLE 1

Phase transition temperatures of
n-C$_q$H$_{2q+1}$O—C$_6$H$_4$—C$_6$H$_4$—COO—C$_6$H$_4$—COO—C*H(CF$_3$)(CH$_2$)$_5$OC$_2$H$_5$

| Example No. | q. | Phase transition temperatures |
|---|---|---|
| 3 | 9 | 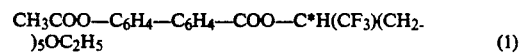 |
| 4 | 12 | 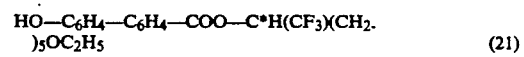 |

SX is unidentified liquid crystal phase.

EXAMPLE 5

Production of 4-(1-trifluoromethyl-6-ethoxyhexyloxycarbonylphenyl) 4'-n-decylbiphenyl-4-carboxylate (In formula (II), R=C$_{10}$H$_{21}$, X=-(single bond), K=2, L=1, m=5, n=2)

Figure 4:
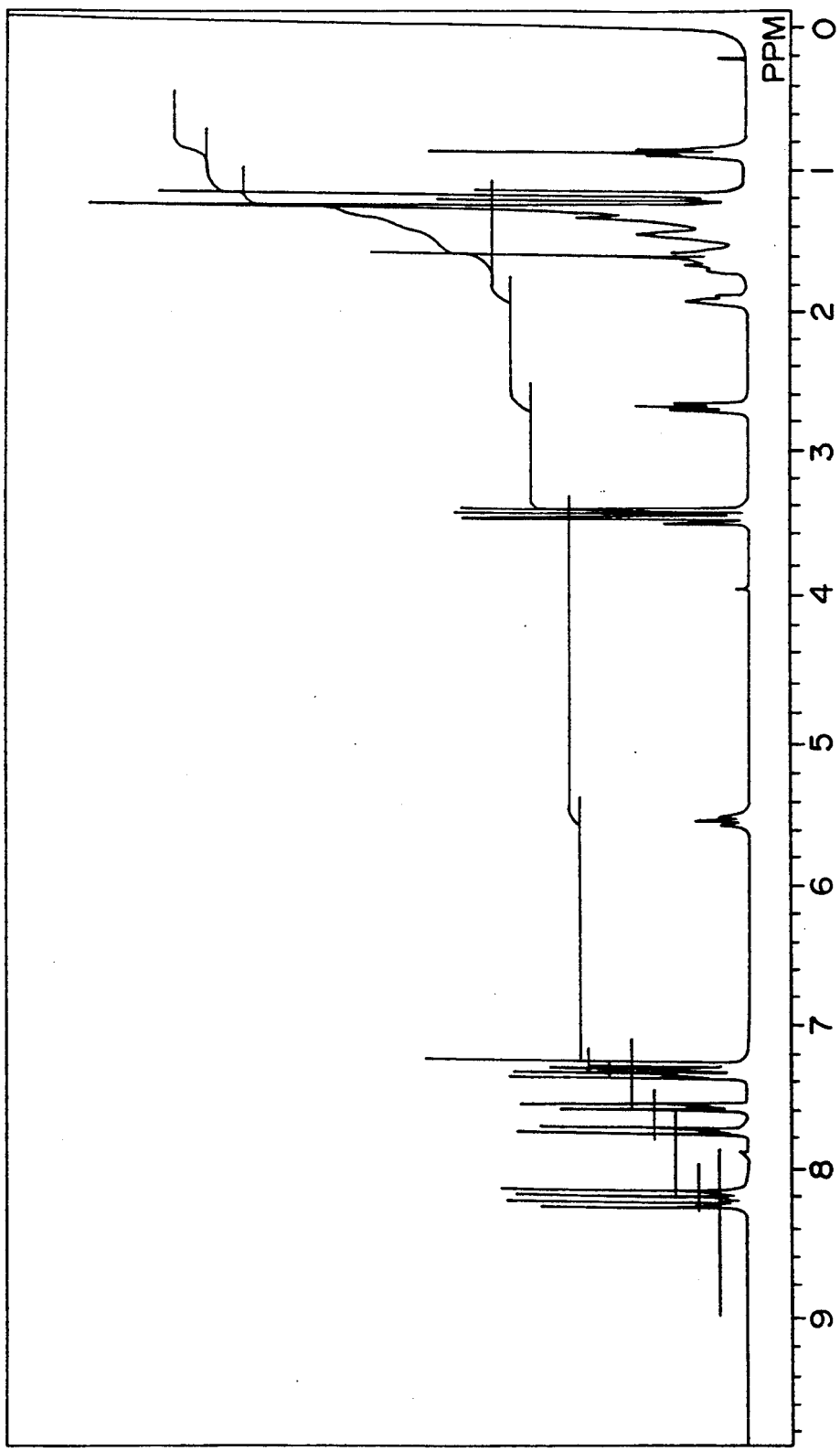
FIGS. 4, 5, 6, 7 and 8 are NMR spectra of liquid crystal compounds in Examples 5, 6, 7, 8 and 9, respectively.

A final compound was produced in the same way as in Example 2 except using 4'-decylbiphenyl-4-carboxylic acid instead of 4'-octyloxybiphenyl-4-carboxylic acid. An NMR spectrum of the final compound is shown in FIG. 4. Identification of phases was carried out by observation of a texture and measurement with DSC. As a result, the following phase transition temperatures are shown. An antiferroelectric phase and also a chiral smectic C phase (S$_{C*}$) being a ferroelectric phase were observed.

uct.

2) Production of 4'-hydroxy-4-(1-trifluoromethyl-6-ethoxyhexyloxycarbonyl)bihpenyl (2)

HO—C$_6$H$_4$—C$_6$H$_4$—COO—C*H(CF$_3$)(CH$_2$)$_5$OC$_2$H$_5$     (21)

To the compound (1) produced above were added 15 ml of ethanol and 1.2 g of benzylamine, and the mixture was stirred at room temperature for 24 hours. Fifty milliliters of dichloromethane were added, and the resulting mixture was washed with hydrochloric acid and water. After drying, the solvent was removed, and the residue was purified by silica gel column chromatography to obtain 2.1 g of a final product.

3) Production of 4-(1-trifluoromethyl-6-ethoxyhexyloxycarbonylbiphenyl) 4'-octylbenzoate (3)

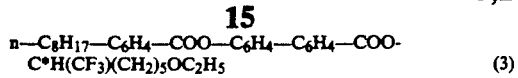
n—C₈H₁₇—C₆H₄—COO—C₆H₄—C₆H₄—COO-
C*H(CF₃)(CH₂)₅OC₂H₅                              (3)

One gram of p-octylbenzoic acid was chlorinated with 10 ml of thionyl chloride in the same way as in 1). To the resulting acid chloride were added 20 ml of toluene and 4 ml of pyridine. One gram of the compound (2) was further added. The mixture was refluxed for about 10 hours with heating, and left to cool, followed by adding 50 ml of dichloromethane. The mixture was washed with hydrochloric acid, a sodium hydroxide aqueous solution and water in this sequence, and dried. Then, the solvent was removed, and the residue was purified by silica gel column chromatography to obtain 0.5 g of a final product.

Figure 5:
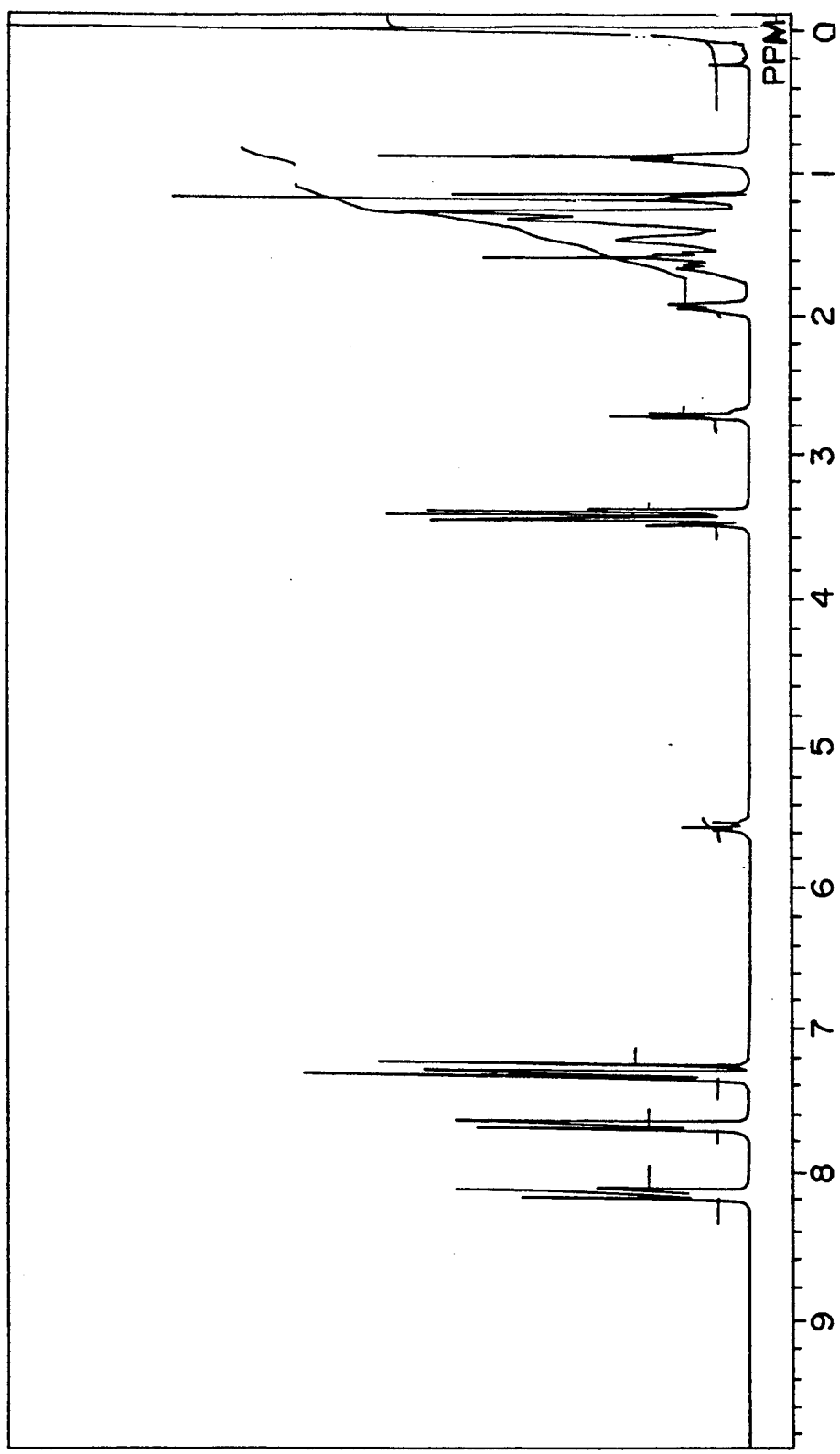

An NMR spectrum of the final product is shown in FIG. 5. Identification of phases was carried out by observation of a texture and measurement with DSC.

Phase transition temperatures of the compound (3) of this application are as follows.

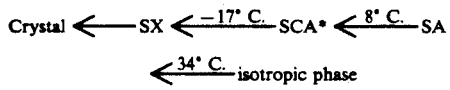

4) Optical response of this compound was measured as in 5) of Example 2. As a result, a double hysteresis peculiar to an antiferroelectric phase was shown.

EXAMPLE 7

Production of 4-(1-trifluoromethyl-6-ethoxyhexyloxycarbonylbiphenyl) 4'-octyloxybenzoate (In formula (II), R=C₈H₁₇, X=0, K=1, L=2, m=5, n=2)

Figure 6:
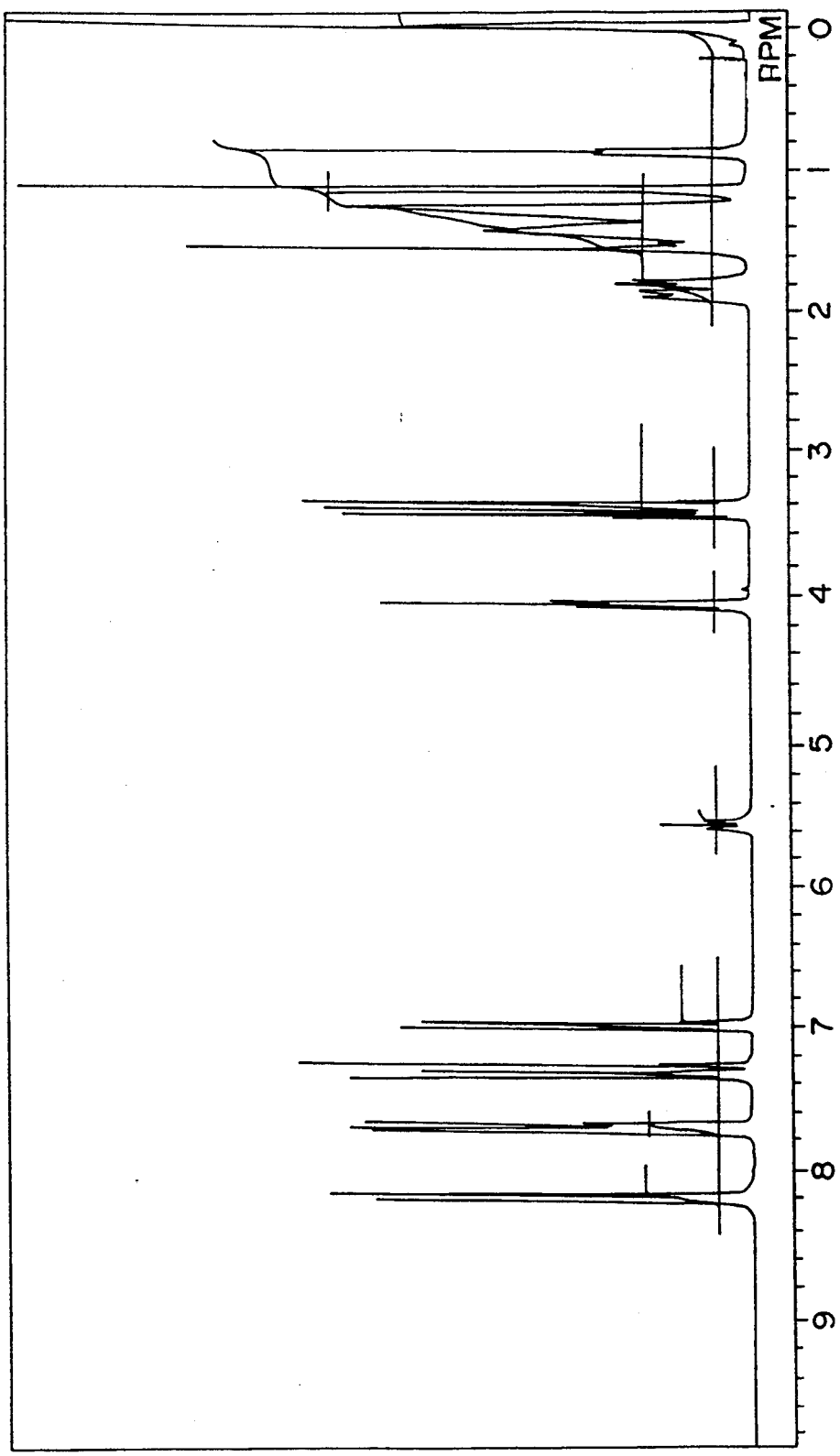

A final product was produced as in Example 6 except that p-octylbenzoic acid was replaced with p-octyloxybenzoic acid. An NMR spectrum of the final product is shown in FIG. 6. Identification of phases was conducted by observation of a texture and measurement with DSC. As a result, the following phase transition temperatures were shown and an antiferroelectric phase was observed.

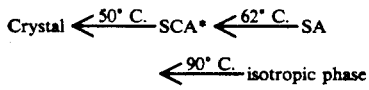

Optical response of this compound was measured as in 5) of Example 2, and consequently, a double hysteresis peculiar to the antiferroelectric phase was shown.

EXAMPLE 8

Production of 4-(1-trifluoromethyl-6-ethoxyhexyloxycarbonylbiphenyl) 4'-octyloxybiphenyl-4-carboxylate (In formula (II), R=C₈H₁₇, X=0, K=2, L=2, m=5, n=2)

Figure 7:
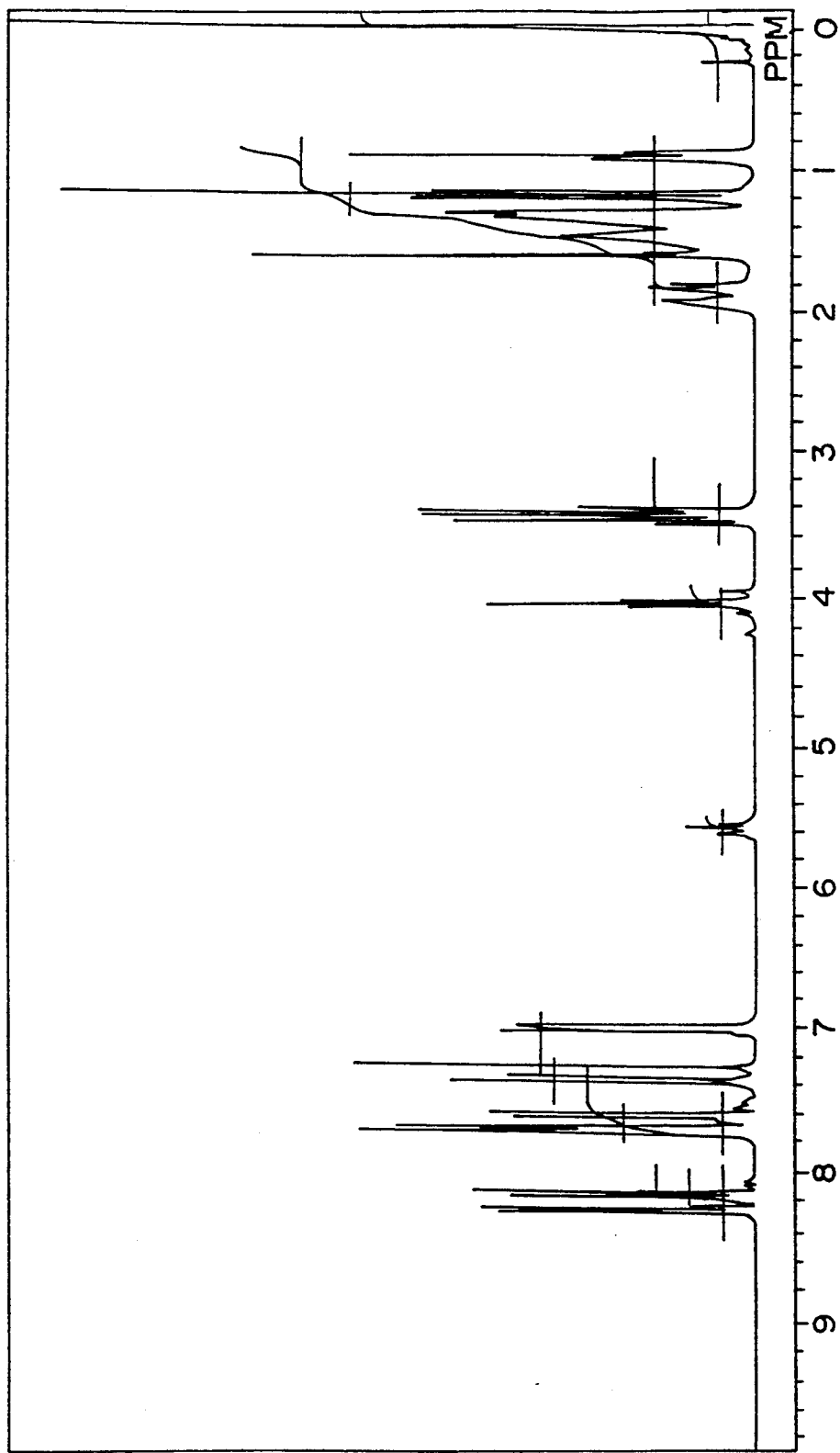
Figure 8:
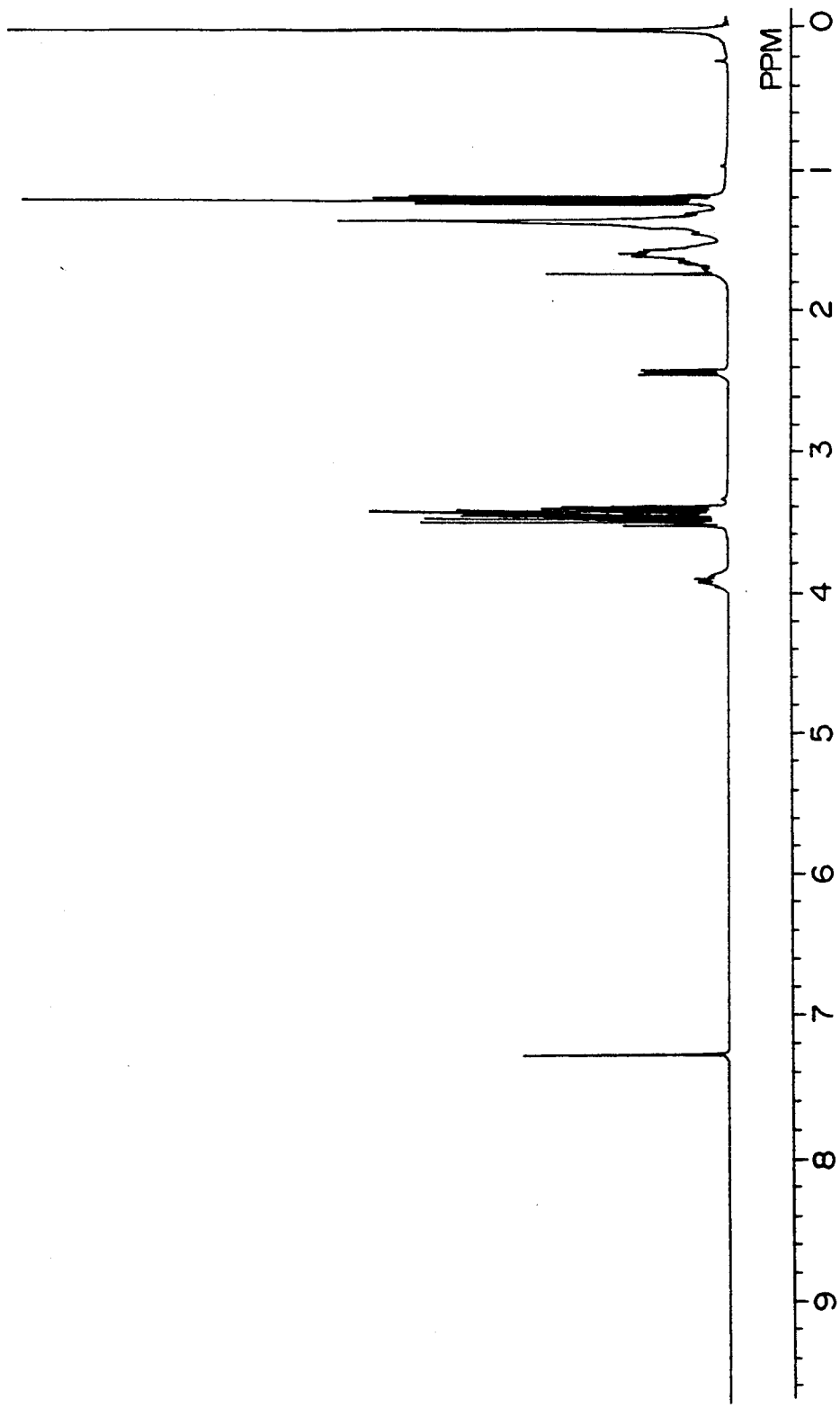

Using 4'-octyloxybiphenyl-4-carboxylic acid formed in Example 2 and 4'-hydroxy-4-(1-trifluoromethyl-6-ethoxyhexyloxycarbonyl)biphenyl formed in Example 6, a final product was produced as in Example 2. An NMR spectrum of the final product is shown in FIG. 7. Identification of phases was carried out by observation of a texture and measurement with DSC. As a result, the following phase transition temperatures were shown and an antiferroelectric phase was observed.

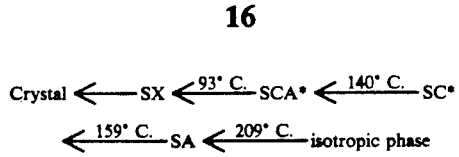

EXAMPLE 9

Production of R-(+)-1,1,1-trifluoro-9-ethoxy-2-nonanol (In formula (1), m=7, n=2)

(1) A sulfonic acid ester of 4,4,4-trifluoro-3-tetrahydropyranyloxybutyl alcohol was produced as in Example 1.

(2) Production of 1,1,1-trifluoro-9-ethoxy-2-tetrahydropyranyloxynonane

In the same way as in (5) of Example 1, 1,1,1-trifluoro-9-ethoxy-2-tetrahydropyranyloxynonane was produced except that 3-ethoxy-1-bromopropane was replaced with 5-ethoxy-1-bromopentane. Yield 65%.

(3) Production of 1,1,1-trifluoro-9-ethoxy-2-nonanol

In the same way as in (6) of Example 1, 1,1,1-trifluoro-9-ethoxy-2-nonanol was produced except that 1,1,1-trifluoro-7-ethoxy-2-tetrahydropyranyloxyheptane was replaced with 1,1,1-trifluoro-9-ethoxy-2-tetrahydropyranyloxynonane. Purity 89%, yield 87% and [α]₀²⁶ = +11°. (C=1.2, CHCl₃).

What we claim is:

1. A liquid crystal compound represented by formula (II)

$$R-X-(C_6H_4)_K-COO-(C_6H_4)_L-COO-C^*H(CH_2)_mOC_nH_{2n+1} \quad (II)$$
$$| \atop CF_3$$

wherein R denotes a linear alkyl group having 6 to 14 carbon atoms, X denotes a single bond or an oxygen atom, K and L are independently 1 or 2, m is an integer of 5 to 7, n is an integer of 1 to 4, and C* denotes an asymmetric carbon atom.

2. The liquid crystal compound of claim 1 wherein R in formula II is a linear alkyl group having 8 to 12 carbon atoms.

3. The liquid crystal compound of claim 1 wherein m is 5.

4. The liquid crystal compound of claim 3 wherein n is 2 or 3.

5. The liquid crystal compound of claim 1 wherein X is a single bond.

6. The liquid crystal compound of claim 1 wherein X is an oxygen atom.

7. The liquid crystal compound of claim 1 wherein R represents C₆H₁₇, X is an oxygen atom, K is 2, L is 1, m is 5 and n is 2.

8. The liquid crystal compound of claim 1 wherein R is a linear alkyl group having 9 or 12 carbon atoms, X is an oxygen atom, K is 2, L is 1, m is 5 and n is 2.

9. The liquid crystal compound of claim 1 wherein R is a linear alkyl group having 10 carbon atoms, X is a single bond, K is 2, L is 1, m is 5 and n is 2.

10. The liquid crystal compound of claim 1 wherein R is a linear alkyl group having 8 carbon atoms, X is a single bond, K is 2, L is 2, m is 5 and n is 2.

11. The liquid crystal compound of claim 1 wherein R is a linear alkyl group having 8 carbon atoms, X is an oxygen atom, K is 1, L is 2, m is 5 and n is 2.

12. The liquid crystal compound of claim 1 wherein R is a linear alkyl group having 8 carbon atoms, X is an oxygen atom, K is 2, L is 1, m is 5 and n is 2.

* * * * *